(12) United States Patent
Cerchietti (10) Patent No.: US 8,729,133 B2
(45) Date of Patent: May 20, 2014

(54) METHOD FOR TREATING CANCER (75) Inventor: Leandro Carlos A Cerchietti, New York, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 11/705,964

(22) Filed: Feb. 14, 2007

(65) Prior Publication Data

US 2007/0203249 A1    Aug. 30, 2007

Related U.S. Application Data (60) Provisional application No. 60/743,372, filed on Feb. 28, 2006.

(51) Int. Cl.
*A61K 31/131* (2006.01)

(52) U.S. Cl.
USPC .......................................... 514/673; 514/565

(58) Field of Classification Search
None
See application file for complete search history.

(56) References Cited

U.S. PATENT DOCUMENTS

| | | | | |
|---|---|---|---|---|
| 3,291,689 | A * | 12/1966 | Nordmann ..................... | 514/565 |
| 5,231,085 | A * | 7/1993 | Alexander et al. .............. | 514/44 |
| 5,554,638 | A * | 9/1996 | Dewhirst et al. ............... | 514/398 |
| 6,015,798 | A * | 1/2000 | Ogilvie et al. .................. | 514/57 |
| 6,599,878 | B2 * | 7/2003 | Rooney ............................. | 514/6 |
| 6,812,003 | B2 * | 11/2004 | Dalton et al. ................... | 435/69.1 |
| 2005/0036949 | A1 * | 2/2005 | Tucker et al. ................... | 424/45 |
| 2005/0036994 | A1 * | 2/2005 | Mihara et al. .............. | 424/93.21 |
| 2005/0288373 | A1 * | 12/2005 | Ron ............................... | 514/565 |

OTHER PUBLICATIONS

Heys et al. Dietary supplementation with L-arginine: modulation of tumour-infiltrating lymphocytes in patients with colorectal cancer. Br. J. surg. 1997; 84(2):238-41, abstract only.*
Brittenden et al., Br. J. Cancer, 1994, 69, 918-921.*
IRSA, http://www.irsa.org/radation_therapy.html, pdf provided, 2003, 3 pages.*
Ersin et al., J. Surgical Research, 89, 2000, 121-125.*
Cho-Chung, Y.S., Clair, T., Bodwin, J.S. & Hill, D.M., "Arrest of mammary tumor growth in vivo by L-arginine: stimulation of NAD-dependent activation of adenylate cyclase," Biochemical and Biophysical Research Communications, 1980, vol. 95, No. 3; pp. 1306-1313.
Cho-Chung, Y.S., Clair, T., Bodwin, J.S. & Berghoffer, B., "Growth arrest and morphological change of human breast cancer cells by dibutyryl cyclic AMP and L-arginine," Science, 1981, vol. 214; pp. 77-79.
Dani, N., et al., "Combining affinity purification by ADP-ribose-binding macro domains with mass spectrometry to define the mammalian ADP-ribosyl proteome," Proceedings of the National Academy of Science USA, 2009, vol. 106, No. 11; pp. 4243-4248.
Haigis, M.C., et al., "SIRT4 inhibits glutamate dehydrogenase and opposes the effects of calorie restriction in pancreatic beta cells," Cell, 2006, vol. 126; pp. 941-954.
Pancholi, V. & Fischetti, V.A., "Glyceraldehyde-3-phosphate dehydrogenase on the surface of group A *Streptococci* is also an ADP-ribosylating enzyme," Proceedings of the National Academy of Science USA, 1993, vol. 90; pp. 8154-8158.
Brune, B. & Mohr, S., "Protein thiol modification of glyceraldehyde-3-phosphate dehydrogenase and caspase-3 by nitric oxide," Current Protein and Peptide Science, 2001, vol. 2, No. 1; pp. 61-72.
Rodriguez-Enriquez, S., et al., "Energy metabolism transition in multi-cellular human tumor spheroids," Journal of Cellular Physiology, 2008, vol. 216; pp. 189-197.
Walenta, S. & Mueller-Klieser, W.F., "Lactate: mirror and motor of tumor malignancy," Seminars in Radiation Oncology, 2004, vol. 14, No. 3; pp. 267-274.
Quennet, V., et al., "Tumor lactate content predicts for response to fractionated irradiation of human squamous cell carcinomas in nude mice," Radiotherapy and Oncology, 2006, vol. 81; pp. 130-135.
Gatenby, R.A. & Gillies, R.J., "Why do cancers have high aerobic glycolysis?" Nature Reviews Cancer, 2004, vol. 4; pp. 891-899.
Chernov, M.F., Hayashi, M., Izawa, M., Ono, Y. & Hori, T., "Proton magnetic resonance spectroscopy (MRS) of metastatic brain tumors: variations of metabolic profile," International Journal of Clinical Oncology, 2006, vol. 11; pp. 375-384.
Howe, F.A., et al., "Metabolic profiles of human brain tumors using quantitative in vivo 1H magnetic resonance spectroscopy," Magnetic Resonance in Medicine, 2003, vol. 49; pp. 223-232.
Cook, T., et al., "Nitric oxide and ionizing radiation synergistically promote apoptosis and growth inhibition of cancer by activating p53," Cancer Research, 2004, vol. 64; pp. 8015-8021.
Wang, Z., et al., "Adenoviral gene transfer of the human inducible nitric oxide synthase gene enhances the radiation response of human colorectal cancer associated with alterations in tumor vascularity," Cancer Research, 2004, vol. 64; pp. 1386-1395.
Jordan, B.F., et al., "Nitric oxide as a radiosensitizer: evidence for an intrinsic role in addition to its effect on oxygen delivery and consumption," International Journal of Cancer, 2004, vol. 109; pp. 768-773.
Nielsen, F.U., et al., "Localized in vivo 1H NMR spectroscopy of murine tumours: effect of blood flow reduction," NMR in Biomedicine, 1999, vol. 12; pp. 175-183.
Castillo, L., et al., "Dietary arginine uptake by the splanchnic region in adult humans," American Journal of Physiology, 1993, vol. 265; pp. E532-E539.
Castillo, L., Beaumier, L., Ajami, A.M. & Young, V.R., "Whole body nitric oxide synthesis in healthy men determined from [15N]arginine-to-[15N]citrulline labeling," Proceedings of the National Academy of Science USA, 1996, vol. 93; pp. 11460-11465.

* cited by examiner

*Primary Examiner* — Kyle Purdy
(74) *Attorney, Agent, or Firm* — Ascenda Law Group PC (57) ABSTRACT

This invention relates to a process of treating/affecting cancers that are particularly susceptible to radiation therapy by administering to a host in need of such treatment an amino acid and radiation therapy.

15 Claims, 4 Drawing Sheets

Figure 1. Overall survival (p=0.035, Cox Mantel Test).

Median survival for placebo = 2 months (1-3 months) and for L-Arginine = 8 months (7-9 months)

Figure 2

Lactate levels in tumors.

Figure 3. Lactate levels measured by NMR spectroscopy in patients treated with L-Arginine or placebo.

3. I. NMR Spectroscopy 15 60 minutes before (A) and after (B) a 10 mg dose of L-Arginine (pink arrow indicates lactate peak)

Figure 3 (continued)
3. II. NMR Spectroscopy 15 60 minutes before (A) and after (B) Placebo (white arrow indicates lactate peak)

METHOD FOR TREATING CANCER

RELATED APPLICATIONS

This application claims the benefit under 35 U.S.C. 119(e) of U.S. Provisional Application Ser. No. 60/743,372, filed Feb. 28, 2006, which is incorporated herein by reference and made a part hereof.

FIELD OF INVENTION

This invention relates to a process of treating/affecting cancers that are particularly susceptible to radiation therapy.

BACKGROUND OF THE INVENTION

Cancers are one of the leading causes of death in humans. The exact cause of cancer is not known. There is evidence that certain activities, such as smoking or exposure to carcinogens, may enhance the risk for certain types of cancers and tumors. Treatment of cancer in the early stages typically comprises local treatment such as, surgery and/or radiotherapy. While radiation therapy has been widely used in managing cancer, it is limited by lack of radiosensitivity of specific regions of malignant tumors. More advanced disease is treated by combining local treatment with chemotherapy. Although current chemotherapeutic agents have been shown to be effective against cancers and tumor cells, the use of combined treatment with all three modalities, surgery, radiotherapy, and chemotherapy, have not been shown to be effective against all cancer and tumor cells.

Significant effort in cancer therapeutics is also focused on cancers that are metastasized. About 40% of patients with advanced cancer develop metastases in the central nervous system, mainly from primary tumors of lung, breast and melanoma. In most cases there can be multiple CNS metastases, thereby adversely affecting surgery or localized radio-surgery. The current standard of care for these patients is radiation therapy, which can improve neurological symptoms but does not have any impact on patient's overall survival. Although over half of all cancer patients receive radiation therapy during treatment (Owen et al. *Int J Radiat Oncol Biol Phys* 24, 983-986, 1992), a need remains to improve the cure rate by radiation therapy alone. Radiotherapy has been the mainstay of treatment for most patients with unresectable brain metastases. Considering the time to non-CNS death, even in the case of uncontrolled primary and/or the presence of extracranial metastases, for selected patients (i.e. with Karnofsky Functional Index ≥70%) the outcome can be improved by achieving greater local control.

One approach to improve the intracranial control is to administer agents that enhance the sensitivity of cancer cells to irradiation. It has been surprisingly found that administering L-Arginine before radiation shows a surprising increase in tumor blood flow and decrease in glucose uptake, thereby decreasing tumor hypoxia and lactate production. This in turn can increase the tumoricidal effect of radiotherapy.

SUMMARY OF THE INVENTION

The present invention provides a method of treating cancer in a mammal. The present invention also provides a method of treating a brain lesion in a mammal. The present invention also provides a method of affecting metabolic pathway of a brain lesion in a mammal. Such methods include administering to a mammal in need of such treatment a therapeutically effective amount (e.g., at least about 0.5 grams) of an amino acid, followed by radiation therapy.

The present invention also provides a method of affecting metabolic pathway of cancer in a mammal. The present invention also provides a method of reducing lactate levels in a tumor in a mammal. The present invention also provides a method of reducing lactate levels in brain lesions in a mammal. Such methods include administering to a mammal in need of such treatment a therapeutically effective amount (e.g., at least about 0.5 grams) of an amino acid.

The mammal can be administered at least about 2 gm, at least about 5 gm, from about 7 gm to about 15 gm, or about 10 gm of an amino acid. Alternatively, the mammal can be administered in at least about 0.0025 gram of amino acid per kilogram of body mass, up to about 1.5 gram of amino acid per kilogram of body mass, or from about 0.0025 gram of amino acid per kilogram of body mass to about 1.5 gram of amino acid per kilogram of body mass.

The amino acid can be administered at least about 1 minute prior to, at least about 5 minutes prior to, up to about 120 minutes prior to, 60 minutes prior to, up to about 30 minutes prior to, or from about 5 minutes to about 120 minutes prior to administering radiation therapy.

The amino acid can be administered at least once per day, up to about seven times per week, or up to about twice per week. Additionally, the administration can be carried out for at least one day, at least about one week, at least about one month, or at least about six months.

The amino acid can be L-Arginine, or a pharmaceutically acceptable salt thereof. Specifically, the amino acid can be L-Arginine hydrochloride. Specifically, the amino acid can be L-Arginine monochlorohydrate. Additionally, the amino acid can be orally administered.

The cancer can be a type that is susceptible to be treated with radiation therapy. Specifically, the cancer can be bladder cancer, breast cancer, cervical cancer, esophageal cancer, head and neck cancer, laryngeal cancer, lung cancer, ovarian cancer, brain metastases, pancreatic cancer, prostate cancer, rectal cancer, skin cancer, testicular cancer, uterine cancer, or a brain tumor. More specifically, the cancer can be brain metastases, breast cancer, brain tumor or lung cancer. More specifically, the cancer can be brain metastases. Alternatively, the cancer can be lung cancer. Alternatively, the cancer can be breast cancer.

BRIEF DESCRIPTION OF THE FIGURES

FIG. 2.

FIG. 3.I: This figure shows the actual NMR peak for lactate in a brain metastasis before and after administering about 10 grams of L-Arginine orally. The arrow points to the peak in the NMR spectra that corresponds to lactate. FIG. 3.I.B shows the decrease in the peak corresponding to lactate in the tumor as seen about 60 minutes after administering L-Arginine when compared to the peak in the NMR spectra corresponding to lactate in the tumors before administering L-Arginine as seen in FIG. 3.I.A. Both FIGS. 3.II.A and B also provide a scan of the whole brain with the tumor location marked by a square.

FIG. 3.II: This figure shows the actual NMR peak for lactate in a brain metastasis before and after administering placebo. The arrow points to the peak in the NMR spectra that corresponds to lactate. FIG. 3.II.B shows the peak corresponding to lactate in the tumor as seen about 60 minutes after administering placebo when compared to the peak in the NMR spectra corresponding to lactate in the tumors before administering placebo as seen in FIG. 3.II.A. The intensity of the peak, corresponding to lactate, in the NMR spectra before and after administering placebo do not show any appreciable decrease in the lactate levels in tumors. Both FIGS. 3.II.A and B also provide a scan of the whole brain with the tumor location marked by a square.

DETAILED DESCRIPTION OF THE INVENTION

Definitions

Figure 1:
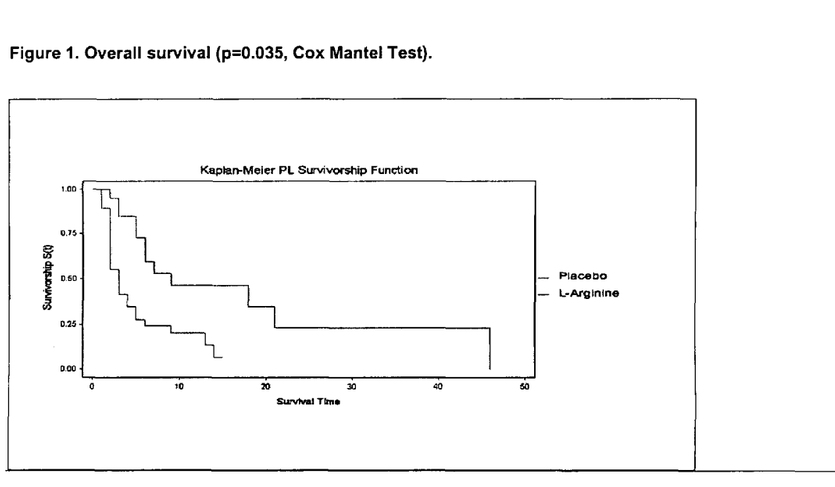
FIG. 1: This figure shows the Kaplan-Meier graph which shows the median survival time for patients with brain metastases who were given a placebo and patients who received about 10 grams of L-Arginine orally. The median survival time for patients who received the placebo was 2 months while the median survival time for patients who received L-Arginine was 8 months.
Figure 2:
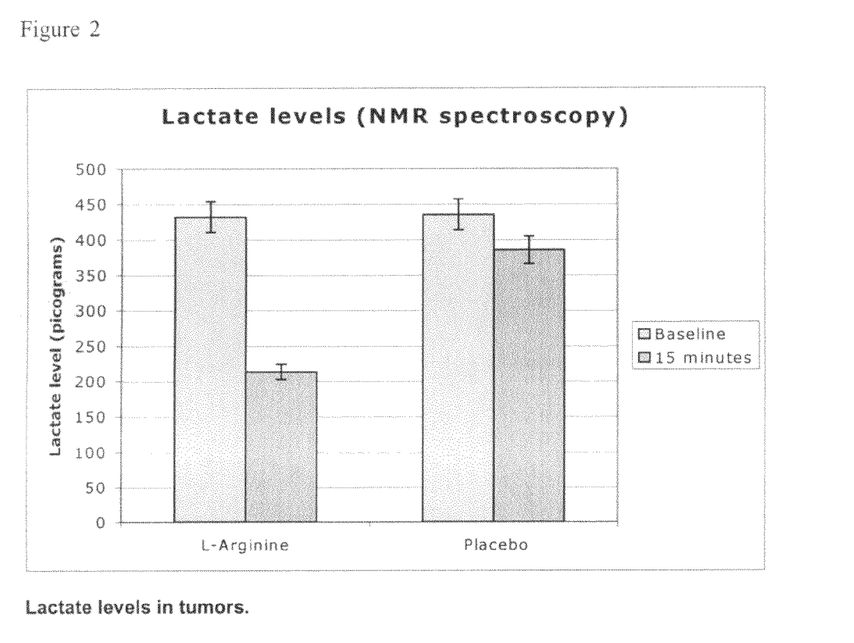
FIG. 2 shows lactate levels in brain metastases tumors before and after administering about 10 grams of L-Arginine orally. Lactate levels in tumors for the group that received L-Arginine dropped about 50% about 60 minutes after administering L-Arginine. Lactate levels in tumors for the group that received placebo showed an insignificant drop (about 10%) about 60 minutes after administering a placebo. Lactate levels, before and after administering L-Arginine and placebo respectively, were measured by Nuclear Magnetic Spectroscopy (NMR).
Figure 3:
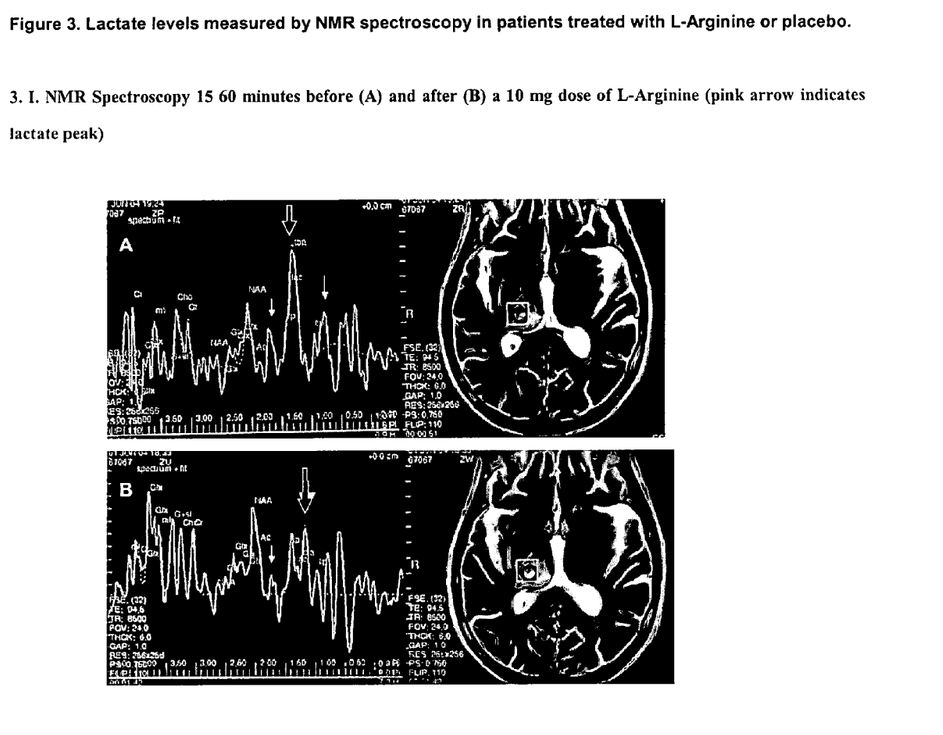

Unless stated otherwise, the following terms and phrases as used herein are intended to have the following meanings:

The term "amino acid," comprises the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also comprises natural and unnatural amino acids bearing a conventional amino protecting group (e.g. acetyl or benzyloxycarbonyl), as well as natural and unnatural amino acids protected at the carboxy terminus (e.g. as a ($C_1$-$C_6$)alkyl, phenyl or benzyl ester or amide; or as an α-methylbenzyl amide). The term also includes polymeric forms of the amino acid, e.g., poly-L-arginine, poly-L-lysine, etc. Other suitable amino and carboxy protecting groups are known to those skilled in the art (See for example, Greene, T. W.; Wutz, P. G. M. "Protecting Groups In Organic Synthesis" second edition, 1991, New York, John Wiley & sons, Inc., and references cited therein).

As used herein, arginine (Arg) includes L-Arginine hydrochloride (L-arginine monochlorhydrate, L-A-HCl); which is chemically designated as S(+)-2-Amino-5-[(aminoiminomethyl)amino]pentanoic acid monohydrochloride. The structural formula is shown below.

L-Arginine hydrochloride

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the compounds useful in the present invention can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., p. 1418 (1985), the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

"Therapeutically effective amount" is intended to include an amount of a compound useful in the present invention or an amount of the combination of compounds claimed, e.g., to treat or prevent the disease or disorder, or to treat the symptoms of the disease or disorder, in a host. The combination of compounds is preferably a synergistic combination. Synergy, as described for example by Chou and Talalay, Adv. Enzyme Regul. 22:27-55 (1984), occurs when the effect of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased activity, or some other beneficial effect of the combination compared with the individual components.

As used herein, "treating" or "treat" includes (i) preventing a pathologic condition from occurring (e.g. prophylaxis); (ii) inhibiting the pathologic condition or arresting its development; (iii) relieving the pathologic condition; and/or diminishing symptoms associated with the pathologic condition.

The amino acids described herein can be administered as the parent compound, a pro-drug of the parent compound, or an active metabolite of the parent compound.

"Pro-drugs" are intended to include any covalently bonded substances which release the active parent drug or other formulas or compounds of the present invention in vivo when such pro-drug is administered to a mammalian subject. Pro-drugs of a compound of the present invention are prepared by modifying functional groups present in the compound in such a way that the modifications are cleaved, either in routine manipulation in vivo, to the parent compound. Pro-drugs include compounds of the present invention wherein the carbonyl, carboxylic acid, hydroxy or amino group is bonded to any group that, when the pro-drug is administered to a mammalian subject, cleaves to form a free carbonyl, carboxylic acid, hydroxy or amino group. Examples of pro-drugs include, but are not limited to, acetate, formate and benzoate derivatives of alcohol and amine functional groups in the compounds of the present invention, and the like.

Pro-drugs include hydroxyl and amino derivatives well-known to practitioners of the art, such as, for example, esters prepared by reaction of the parent hydroxyl compound with a suitable carboxylic acid, or amides prepared by reaction of the parent amino compound with a suitable carboxylic acid. Simple aliphatic or aromatic esters derived from hydroxyl groups pendent on the compounds employed in this invention are preferred pro-drugs. In some cases it may be desirable to prepare double ester type pro-drugs such as (acyloxy) alkyl esters or ((alkoxycarbonyl)oxy)alkyl esters. Specific suitable esters as pro-drugs include methyl, ethyl, propyl, isopropyl, n-butyl, isobutyl, tert-butyl, and morpholinoethyl.

*Hydrolysis in Drug and Pro-drug Metabolism: Chemistry, Biochemistry, and Enzymology*, by Bernard Testa and Joachim Mayer; Vch Verlagsgesellschaft Mbh (August 2003) provides a comprehensive review of metabolic reactions and enzymes involved in the hydrolysis of drugs and pro-drugs. The text also describes the significance of biotransformation and discusses the physiological roles of hydrolytic enzymes, hydrolysis of amides, and the hydrolysis of lactams. Additional references useful in designing pro-drugs employed in the present invention include, e.g., *Biological Approaches to the Controlled Delivery of Drugs* (Annals of the New York Academy of Sciences, Vol. 507), R. L. Juliano (editor) (February 1988); *Design of Biobiological agent Properties through Pro-drugs and Analogs*, Edward B. Roche (editor), Amer Biological agent Assn (MacK) (June 1977); *Pro-drugs: Topical and Ocular Drug Delivery* (Drugs and the Biological agent Sciences, Vol. 53), Kenneth B. Sloan (editor), Marcel Dekker (Mar. 17, 1992); *Enzyme-Pro-drug Strategies for Cancer Therapy*, Roger G. Melton (editor), Richard J. Knox (editor), Plenum Press (February 1999); *Design of Pro-drugs*, Hans Bundgaard (editor), Elsevier Science (February 1986); *Textbook of Drug Design and Development*, Povl Krogsgaard-Larsen, Hans Bundgaard (editor), Hardwood Academic Pub (May 1991); *Conversion of Non-Toxic Pro-drugs to Active, Anti-Neoplastic Drugs Selectively in Breast Cancer Metastases*, Basse, Per H. (September 2000); and *Marine lipids for produrgs, of compounds and other biological agent applications*, M. Masson, T. Loftsson and G. G. Haraldsson, Die Pharmazie, 55 (3), 172-177 (2000).

"Metabolite" refers to any substance resulting from biochemical processes by which living cells interact with the active parent drug or other formulas or compounds of the present invention in vivo, when such active parent drug or other formulas or compounds of the present are administered to a mammalian subject. Metabolites include products or intermediates from any metabolic pathway.

"Metabolic pathway" refers to a sequence of enzyme-mediated reactions that transform one compound to another and provide intermediates and energy for cellular functions. The metabolic pathway can be linear or cyclic.

Methods of Obtaining the Amino Acids

Amino acids can be purchased from a variety of sources, such as Aldrich (Milwaukee, Wis.), Sigma (St. Louis, Mo.), and other sources known to one skilled in the art. Alternatively, the amino acids described herein can be prepared by any of the applicable techniques of organic synthesis. Many such techniques are well known in the art. However, many of the known techniques are elaborated in *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, jr., 1980; Vol. 5, Leroy G. Wade, Jr., 1984; and Vol. 6, Michael B. Smith; as well as March, J., *Advanced Organic Chemistry, Third Edition*, (John Wiley & Sons, New York, 1985), *Comprehensive Organic Synthesis, Selectivity Strategy & Efficiency in Modern Organic Chemistry*. In 9 Volumes, Barry M. Trost, Editor-in-Chief (Pergamon Press, New York, 1993 printing); *Advanced Organic Chemistry, Part B: Reactions and Synthesis*, Second Edition, Cary and Sundberg (1983); *Advanced Organic Chemistry, Reactions, Mechanisms, and Structure*, Second Edition, March (1977); *Protecting Groups in Organic Synthesis*, Second Edition, Greene, T. W., and Wutz, P. G. M., John Wiley & Sons, New York; and *Comprehensive Organic Transformations*, Larock, R. C., Second Edition, John Wiley & Sons, New York (1999).

Obviously, numerous modifications and variations of the present invention are possible in light of the above teachings. It is therefore to be understood that within the scope of the appended claims, the invention may be practiced otherwise than as specifically described herein.

Pharmaceutical Formulations

The amino acids described herein are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the *Handbook of Pharmaceutical Excipients* (1986). Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations, both for veterinary and for human use, of the invention comprise at least one active ingredient, as above defined, together with one or more acceptable carriers therefor and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention include one or more amino acids described herein together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient.

Formulations suitable for aerosol or dry powder administration may be prepared according to conventional methods and may be delivered with other therapeutic agents such as compounds heretofore used in the treatment or prophylaxis of a given condition.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use.

Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Amino acids as described herein can also be formulated to provide controlled release of the active ingredient to allow less frequent dosing or to improve the pharmacokinetic or toxicity profile of the active ingredient. Accordingly, the invention also provided compositions comprising one or more Amino acids as described herein formulated for sustained or controlled release.

Effective dose of active ingredient depends at least on the nature of the condition being treated, toxicity, whether the compound is being used prophylactically (lower doses), the method of delivery, and the pharmaceutical formulation, and will be determined by the clinician using conventional dose escalation studies. It can be expected to be from about 0.0001 to about 100 mg/kg body weight per day. Typically, from about 0.001 to about 10 mg/kg body weight per day. More typically, from about 0.01 to about 5 mg/kg body weight per day. More typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

Routes of Administration

One or more amino acids as described herein (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

Combination Therapy

Amino acids described herein can also used in combination with other active ingredients. Such combinations are selected based on the condition to be treated, cross-reactivities of ingredients and pharmaco-properties of the combination.

It is also possible to combine any compound of the invention with one or more other active ingredients in a unitary dosage form for simultaneous or sequential administration to a patient. The combination therapy may be administered as a simultaneous or sequential regimen. When administered sequentially, the combination may be administered in two or more administrations.

The combination therapy may provide "synergy" and "synergistic effect", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

Specifically, the other active ingredient (i.e., second drug) can include, but is not limited to, one or more: anti-neoplastic agents, anti-cancer agents, and anti-cell proliferation agents.

Anti-cancer or anti-cell proliferation agents include, e.g., nucleotide and nucleoside analogs, such as 2-chloro-deoxyadenosine, adjunct antineoplastic agents, alkylating agents, nitrogen mustards, nitrosoureas, antibiotics, antimetabolites, hormonal agonists/antagonists, androgens, antiandrogens, antiestrogens, estrogen & nitrogen mustard combinations, gonadotropin releasing hormone (GNRH) analogues, progestrins, immunomodulators, miscellaneous antineoplastics, photosensitizing agents, and skin & mucous membrane agents. See, Physician's Desk Reference, 2001 Edition.

Suitable adjunct antineoplastic agents include Anzemet® (Hoeschst Marion Roussel), Aredia® (Novartis), Decadron® (Merck), Deltasone® (Pharmacia), Didronel® (MGI), Diflucan® (Pfizer), Epogen® (Amgen), Ergamisol® (Janssen), Ethyol® (Alza), Kenacort® (Bristol-Myers Squibb), Kytril® (SmithKline Beecham), Leucovorin® (Immunex), Leucovorin® (Glaxo Wellcome), Leucovorin® (Astra), Leukine® (Immunex), Marinol® (Roxane), Mesnex® (Bristol-Myers Squibb Oncology/Immunology), Neupogen (Amgen), Procrit® (Ortho Biotech), Salagen® (MGI), Sandostatin® (Novartis), Zinecard® (Pharmacia & Upjohn), Zofran® (Glaxo Wellcome) and Zyloprim® (Glaxo Wellcome).

Suitable miscellaneous alkylating agents include Myleran® (Glaxo Wellcome), Paraplatin® (Bristol-Myers Squibb Oncology/Immunology), Platinol® (Bristol-Myers Squibb Oncology/Immunology), and Thioplex® (Immunex).

Suitable nitrogen mustards include Alkeran® (Glaxo Wellcome), Cytoxan® (Bristol-Myers Squibb Oncology/Immunology), Ifex® (Bristol-Myers Squibb Oncology/Immunology), Leukeran® (Glaxo Wellcome) and Mustargen® (Merck).

Suitable nitrosoureas include BiCNU® (Bristol-Myers Squibb Oncology/Immunology), CeeNU® (Bristol-Myers Squibb Oncology/Immunology), Gliadel® (Rhône-Poulenc Rover) and Zanosar® (Pharmacia & Upjohn).

Suitable antibiotics include Adriamycin PFS/RDF® (Pharmacia & Upjohn), Blenoxane® (Bristol-Myers Squibb Oncology/Immunology), Cerubidine® (Bedford), Cosmegen® (Merck), DaunoXome® (NeXstar), Doxil® (Sequus), Doxorubicin Hydrochloride® (Astra), Idamycin® PFS (Pharmacia & Upjohn), Mithracin® (Bayer), Mitamycin® (Bristol-Myers Squibb Oncology/Immunology), Nipen® (SuperGen), Novantrone® (Immunex) and Rubex® (Bristol-Myers Squibb Oncology/Immunology).

Suitable antimetabolites include Cytostar-U® (Pharmacia & Upjohn), Fludara® (Berlex), Sterile FUDR® (Roche Laboratories), Leustatin® (Ortho Biotech), Methotrexate® (Immunex), Parinethol® (Glaxo Wellcome), Thioguanine® (Glaxo Wellcome) and Xeloda® (Roche Laboratories).

Suitable androgens include Nilandron® (Hoechst Marion Roussel) and Teslac® (Bristol-Myers Squibb Oncology/Immunology).

Suitable antiandrogens include Casodex® (Zeneca) and Eulexin® (Schering).

Suitable antiestrogens include Arimidex® (Zeneca), Fareston® (Schering), Femara® (Novartis) and Nolvadex® (Zeneca).

Suitable estrogen & nitrogen mustard combinations include Emcyt® (Pharmacia & Upjohn).

Suitable estrogens include Estrace® (Bristol-Myers Squibb) and Estrab® (Solvay).

Suitable gonadotropin releasing hormone (GNRH) analogues include Leupron Depot® (TAP) and Zoladex® (Zeneca).

Suitable progestins include Depo-Provera® (Pharmacia & Upjohn) and Megace® (Bristol-Myers Squibb Oncology/Immunology).

Suitable immunomodulators include Erganisol® (Janssen), Proleukin® (Chiron Corporation), Thalomid® (Celgene Corporation), Revlimid® (Celgene Corporation) and Tetra-hydro-biopterine.

Suitable miscellaneous antineoplastics include Camptosar® (Pharmacia & Upjohn), Celestone® (Schering), DTIC-Dome® (Bayer), Elspar® (Merck), Etopophos® (Bristol-Myers Squibb Oncology/Immunology), Etopoxide® (Astra), Gemzar® (Lilly), Hexalen® (U.S. Bioscience), Hycantin® (SmithKline Beecham), Hydrea® (Bristol-Myers Squibb Oncology/Immunology), Hydroxyurea® (Roxane), Intron A® (Schering), Lysodren® (Bristol-Myers Squibb Oncology/Immunology), Navelbine® (Glaxo Wellcome), Oncaspar® (Rhône-Poulenc Rover), Oncovin® (Lilly), Proleukin® (Chiron Corporation), Rituxan® (IDEC), Rituxan® (Genentech), Roferon-A® (Roche Laboratories), Taxol® (Bristol-Myers Squibb Oncology/Immunology), Taxotere® (Rhône-Poulenc Rover), TheraCys® (Pasteur Merieux Connaught), Tice BCG® (Organon), Velban® (Lilly), VePesid® (Bristol-Myers Squibb Oncology/Immunology), Vesanoid® (Roche Laboratories), Vumon® (Bristol-Myers Squibb Oncology/Immunology) and Nicotinamide.

Suitable photosensitizing agents include Photofrin® (Sanofi).

Specifically, the anti-cancer or anti-cell proliferation agent can include Taxol® (paclitaxol), a niticoxide like compound, or NicOx (NCX-4016).

Taxol® (paclitaxol) is chemically designated as 5β,20-Epoxy-1,2α,4,7β,10β,13α-hexahydroxytax-11-en-9-one 4,10-diacetate 2-benzoate 13-ester with (2R,3S)—N-benzoyl-3-phenylisoserine.

It is appreciated that those skilled in the art understand that the drug useful in the present invention is the biologically active substance present in any of the drugs or agents disclosed above. For example, Taxol® (paclitaxol) is typically available as an injectable, slightly yellow viscous solution. The drug, however, is a crystalline powder with the chemical name 5β,20-Epoxy-1,2α,4,7β,10β,13α-hexahydroxytax-11-en-9-one 4,10-diacetate 2-benzoate 13-ester with (2R,3S)—N-benzoyl-3-phenylisoserine. *Physician's Desk Reference* (*PDR*), Medical Economics Company (Montvale, N.J.), (53rd Ed.), pp. 1059-1067.

Pharmaceutical kits useful in the present invention, which include a therapeutically effective amount of a pharmaceutical composition that includes a compound of component (a) and one or more compounds of component (b), in one or more sterile containers, are also within the ambit of the present invention. Sterilization of the container may be carried out using conventional sterilization methodology well known to those skilled in the art. Component (a) and component (b) may be in the same sterile container or in separate sterile containers. The sterile containers or materials may include separate containers, or one or more multi-part containers, as desired. Component (a) and component (b), may be separate, or physically combined into a single dosage form or unit as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

Imagenologically proven brain metastases: In a patient with history of a cancer with tendency to spread into the CNS, the diagnosis of brain metastases is based in imaging (TC or MRI), with no need for a biopsy or resection (histologically proven).

Histologically proven primary or metastatic cancer: Diagnosis of primary tumors should rely on histology (from a biopsy or surgical resection). The site of origin of a histologically documented carcinoma is not identified clinically in approximately 3% of patients; this situation is often referred to as carcinoma of unknown primary (CUP) origin or occult primary malignancy, therefore only the metastatic disease can be proof by histology.

RPA-RTOG class II: An index from the Recursive Partitioning Analysis of the Radiation Therapy Oncology Group (RPA-RTOG) to classify patients with brain metastases treated with no surgical modalities. RPA-RTOG comprises three different prognostic groups: Class I includes patients with <65 years of age, Kamofsky Functional Index (KFI) ≥70%, with controlled primary tumor and no extra-cranial metastases. Class III includes patients with KFI <70%, and class II consists of patients who do not qualify for class I or III. Further studies confirmed the validity of the RPA-RTOG-derived prognosis parameters as a useful tool to select patients for interventional trials. Those patients belonging to class I seem to be the most likely to profit from aggressive treatments, however their number appears to be very limited (i.e. about 3% in different series). Considering time to non-CNS death, patients in RPA class II might also benefit from increased local control of brain metastases. Measurable brain lesion/s by contrast-enhanced CT or MRI: Lesions that can be accurately measured in at least one dimension with longest diameter equal or greater than 20 mm using conventional techniques. CT (computed tomography) and MRI (magnetic resonance imaging) are the best currently available and reproducible methods to measure target lesions selected for response assessment. To brain lesions, CT should be performed with the administration on a radiological contrast substance. The kinds of side effects patients have and how severe they are, depend on the type and dose of radiotherapy and drugs used in combination, and how patient body reacts. One of the main side effects of radiation is damage to mucoses and bone marrow, which in turn can cause infection, bleeding and cytopenias. To minimize the chance of side effects patients should have adequate bone marrow reservoir and normal hepatic and renal functions. Before starting any treatment patients should complain with these requisites.

Absolute granulocyte count ≥>2000/mm$^3$: Granulocytes are a category of white blood cells, also called polymorphonuclear leukocytes. Granulocytopenia is an abnormally low concentration granulocytes in the blood (less than 2000/mm$^3$). This condition reduces the body's resistance to many infections.

Normal renal function: One of the most important serum markers of renal function is creatinine. Normal values are: serum creatinine <1.5 mg/dL and 24-h creatinine clearance >60 mL/min.

Normal Hepatic function: Normal hepatic function is defined by the serum levels of certain enzymes such as aspartate aminotransferase and alanine aminotransferase. These values should not be higher than 2.5 folds the normal value.

Karnofsky Functional Index: In oncology, performance status is an attempt to quantify cancer patients' general well-being. This measure is used to determine whether they can receive, radiotherapy, chemotherapy, whether dose adjustment is necessary, and as a measure for the required intensity of palliative care. The most generally used are the Kamofsky score and the ECOG/WHO score The Kamofsky score runs from 100 to 0, where 100 is normal health (asymptomatic) and 0 is death. Extra-CNS metastases: Metastases occurring at any site other than the Central Nervous System.

Gray (Gy). One gray is the absorption of one joule of radiation energy by one kilogram of matter. The gray measures the physical effects of radiation. The biological effects can vary by the type and energy of the radiation and the organism and tissues involved.

Any patent, patent document, or reference disclosed herein is incorporated into reference into this invention and forms part of this invention. The present invention can be illustrated by the following non-limiting examples.

EXAMPLES

Experimental

L-Arginine hydrochloride was orally administered five times a week, Monday to Friday, during the radiation therapy (RT) course at a dose of about 10 grams dissolved/mixed with about 100 ml of water and administered to a patient/host from about 15-55 to about 20-65 minutes before each fraction of RT. Radiation therapy was administered to patients using techniques known to one skilled in the art of treating cancer patients. After administering L-Arginine hydrochloride to a patient as discussed above, change in lactate levels in the tumor cells was monitored by localized $^1$H NMR spectroscopy and compared to those who received placebo.

Pharmaceutical Formulations

Illustrative formulations for L-Arginine are shown below.

| 1. Effervescent powder (sachet): | |
|---|---|
| Citric acid monohydrate | 1.2 grams |
| Tartaric acid | 2.24 grams |
| Sodium bicarbonate | 3.4 grams |
| L-arginine monochlorhydrate | 10 grams |
| Lemon flavor | 1 gram |
| Orange flavor | 100 milligrams |
| Sodium saccharin | 20 milligrams |
| 2. Effervescent tablet: | |
| Citric acid | 300 milligrams |
| Sodium bicarbonate | 600 milligrams |
| Gesilite | 50 milligrams |
| Microcrystalline cellulose | 400 milligrams |
| Magnesium stearate | 20 milligrams |
| L-arginine monochlorhydrate | 3.025 grams |
| 3. Solution (bottle) | |
| Ammonium glycyrrhizinate | 142.9 milligrams |
| Sodium saccharin | 71.4 milligrams |
| Methylparaoxybenzoate | 14.3 milligrams |
| Propylparaoxybenzoate | 4.3 milligrams |
| Saccharose | 14.3 milligrams |
| L-arginine monochlorhydrate | 6.05 grams |
| Lemon flavoring | 0.07 milliliters |
| Purified water | up to 20 milliliters |

Patients

Patients with imagenologically proven brain metastases and histologically proven primary or metastatic cancer were eligible for the study. The eligibility criteria included the following: RPA-RTOG class II, measurable brain lesion/s by contrast-enhanced CT or MRI, absolute granulocyte count >2000/mm$^3$, hemoglobin >9 g/L (patients with lower levels were transfused), normal renal (serum creatinine <1.5 mg/dL and 24-h creatinine clearance >60 mL/min) and hepatic functions (aspartate aminotransferase and alanine aminotransferase <2.5 times the upper limit of normal) and no prior treatment for brain metastases. A neurosurgeon examined all eligible patients and their complimentary studies to determine whether their metastases were resectable. Eligible patients with unresectable metastases were randomized.

Study Design and Treatment

The present study was performed in accordance with the ethical standards of the Helsinki Declaration. Within two weeks after the diagnosis of brain metastases, eligible patients were randomly assigned to receive whole brain radiotherapy alone (the control group) or L-Arginine monochlorohydrate (L-Arginine Hydrochloride, L-A-HCl) and whole brain radiotherapy. L-Arginine was orally administered, once a day Monday to Friday, during the radiation therapy (RT) course at a dose of about 10 grams, immediately reconstituted with 100 ml of water and given about 55 to 65 minutes before each fraction of RT.

During RT, all patients were irradiated with $^{60}$Co beams. The whole-brain, of all the individuals enrolled in the study, was treated by two lateral fields to a total dose of 32 Gy in 20 fractions of 1.6 Gy each two times a day with a 6 hours interval between treatments (10 days), followed by a 22.4 Gy boost over the evident lesions with the same fractionation schedule (7 days). The spinal cord dose was limited to 40 Gy.

Patients were administered Dexamethasone (Decadron®, a glucocorticoid drug), which has been used as the principal means of controlling neurological symptoms in patients with brain metastases since the 1960s. In individuals with brain metastases, the volume of brain affected with cerebral edema generally exceeds the volume of tumor. Beneficial symptomatic effects of Dexamethasone are attributed to a reduction in cerebral edema. Dexamethasone is part of the standard of care for patients with brain metastases regardless of any other definite treatment (radiotherapy, surgery). Dexamethasone has many adverse events and are dose-dependent. The lowest dosage of Dexamethasone that maintained patients at their maximum level of comfort and function was sought. For those with no prior usage, a concurrent administration of Dexamethasone was allowed at 4.5 mg/day orally with a slow reduction after radiotherapy. For patients with prior-usage we decreased the dosage until symptoms increased or became apparent; then we increased the dosage until they subsided. For deteriorating patients, rescues with Dexamethasone (orally or intravenous) were allowed and recorded. The use of prophylactic anticonvulsants was not allowed. Dyspepsia was treated with Ranitidine 300 mg/day (Zantac®) and nausea/vomiting with Methoclopramide (Reglan®) as needed.

Initial Assessment and Follow-Up

The baseline evaluation included a complete history and physical examination, brain contrast-enhanced CT scans and/or MRI scans, chest radiographs, blood counts, blood chemistry and electrocardiography. A Mini Mental Status Exam (MMSE) was performed for screening intellectual impairment. During the treatment, patients were to be seen three times a week, then weekly for up to one month after finishing radiotherapy, and then monthly until the patient died. All patients were followed up, by the radiation and medical oncology research physicians, without further treatment.

The following criteria defined radiological response and progression. Complete response was defined as a disappearance of all brain lesions seen on contrast-enhanced CT or MRI scans for at least 1 month. Partial response required at least a 50% decrease in brain lesions for at least 1 month. Stable disease was defined as any brain lesion with shrinkage less than 50% or growth less than 25%. Disease progression was defined as any brain lesion in the brain that enlarged more than 25% or any new brain lesion. For measurable disease, standard bi-perpendicular diameters of the two-dimensional tumor image at maximum dimension were applied.

The following criteria defined symptomatic response and progression. Complete response was defined as disappearance of all neurological-related signs or symptoms seen during a physical exam for at least 1 month, with stable or decreasing steroid dose. Partial response required at least a 50% decrease in all neurological-related sings or symptoms for at least 1 month with a stable or decreasing steroid dose. Stable disease was defined as any neurological-related sing or symptom with alleviation less than 50% or those with no change in intensity. Progressive disease was defined as any increased in the intensity of any sing or symptom, or increased steroid dose, or any new sign or symptom. To assess the symptoms, several 11-point Numerical Rating Scales (NRS) were used.

A "not assessed" response category included patients without a follow-up scan or without symptomatic evaluation. Not assessed patients were considered as progressive disease to determine the overall response rate. Response guidelines as defined by the Eastern Cooperative Oncology Group were used to assess the overall response. The National Cancer Institute common toxicity criteria version 3.0 was used to score treatment adverse events. The principal investigator in consensus with the treatment team made the decision on whether a given adverse event was treatment related (unrelated, unlikely, possible, probable or definite).

Tumor Lactate Determination and Plasma Metabolites

Single-voxel MR spectroscopic data were obtained by using a double-SE point-resolved spectroscopy (PRESS) sequence with one-pulse water signal suppression mainly from metabolically active fleshy parts (contrast-enhanced areas) of the lesions, while avoiding contamination from scalp fat. Appropriate automatic shimming and water suppression were achieved by using 4-8-Hz line width, 1-kHz spectral width, and the automated software developed by the manufacturer. Spectroscopic data from cubic volumes of 1.5× 1.5×1.5-2×2×3 cm were obtained by using the PRESS sequence with 1500/135 ms (TR/TE), 128-256 averages, 1024 data points, and 4000-Hz spectrum width. In most examinations, a voxel size of 2×2×2 cm3 was employed.

The time domain signal intensity was apodized and processed to remove the residual water signal. Post-processing of the spectroscopic data consisted of frequency shift and phase and linear baseline corrections after Fourier transformation. In most cases, these processes were automatic, but where spectra appeared distorted, manual processing was used, particularly for phase and baseline corrections. Frequency domain curve was fitted to Gaussian line shape by using the software provided by the manufacturer to define N-acetylaspartate (NAA), choline-containing components (Cho), and creatine and phosphocreatine (Cr) peaks. Lactate (Lac) peak was calculated at 1.35 ppm (an inverted β-methyl doublet). The lactate assignment was made on the basis of an inverted doublet due to J coupling of lactate-bound protons at a TE of 135 ms. Lactate values were calculated automatically from the area under the peak by using the standard commercial software program provided by the manufacturer.

Biological Results

L-A-HCl was administered (as stated) to 30 patients with unresectable brain metastases. Another 30 patients received placebo. Patients were assessed by brain NMR and/or TC (to asses tumor response) and proton magnetic spectroscopy (to determine the metabolic profile of tumors). Patients who received L-A-HCl showed higher tumoral response rates and survival compared to those who received placebo. By spectroscopy we discovered that orally administering about 10 grams of L-A-HCl favorably modified the metabolic pattern of the tumors in about 60 minutes. During this time, we also noted a decrease in the lactate peak that was used as predictive marker to the therapy, ie., administering radiation therapy.

Statistical Analysis

The primary end point of the study was neurological progression-free survival; secondary end points were response rate, safety, functional independence time, overall survival and tumor lactate peak. Response rate was considered as result of complete response plus partial response over number of patients. Overall, radiological and symptomatic responses were considered. Overall survival and neurological-progression free survival were calculated from the first day of radiotherapy to death or neurological disease progression, respectively; and were analyzed by the Kaplan-Meier method, with the use of two-sided log-rank statistics. All analyses were conducted in an intention-to-treat basis.

Results

TABLE 1

Characteristics of the patients and disease at the moment of inclusion in the study(randomized)

| | RT Alone (n = 31) | RT-Arginine (n = 22) |
|---|---|---|
| Patient Age (mean/range) | 54.5 (29–76) | 54.6 (34–72) |
| Primary Tumor Site | | |
| Lung | 13 | 11 |
| Breast | 9 | 3 |
| Melanoma | 3 | 2 |
| Others | 6 | 6 |
| Karnofsky Functional Index | | |
| 70% | 16 | 11 |
| 80% | 11 | 5 |
| 90% | 4 | 6 |
| Time Interval to BM (from initial diagnosis of primary cancer) | | |
| <2 years | 23 | 19 |
| >2 years | 8 | 3 |
| Headache | | |
| Absent | 20 | 8 |
| Present | 11 | 14 |
| Neurologic Function | | |
| No Dysfunction | 8 | 7 |
| Some Dysfunction | 23 | 15 |
| Number of Lesions | | |
| Solitary | 14 | 8 |
| Multiple | 17 | 14 |
| Status of Primary Tumor | | |
| Controlled | 6 | 2 |
| Uncontrolled | 25 | 20 |
| Brain Metastases | | |
| Alone | 10 | 9 |
| Extra-CNS metastases | 21 | 13 |
| Sentinel Lesion Location | | |
| Supratentorial | 26 | 19 |
| Infratentorial | 5 | 3 |

Data presented as number of patients.

TABLE 2

Efficacy

| | RT Alone (n = 31) | RT-Arginine (n = 22) | P value |
|---|---|---|---|
| Symptomatic Response | | | |
| Total responses | 16 (51%) | 21 (95%) | |
| Complete | 11 | 20 | |
| Partial | 5 | 1 | |
| Stable Disease | 2 (7%) | 1 (5%) | |
| Progressive Disease | 13 (42%) | 0 (0%) | 0.023 |
| Radiologic Response | | | |
| Not assessed | 10 (33%) | 1 (5%) | |
| Total responses | 7 (22%) | 18 (81%) | |
| Complete | 3 | 6 | |
| Partial | 4 | 13 | |
| Stable Disease | 9 (29%) | 2 (9%) | |
| Progressive Disease | 5 (16%) | 0 | 0.012 |
| Overall Response | | | |
| Total responses | 7 (22%) | 18 (81%) | |
| Complete | 3 | 6 | |

TABLE 2-continued

| | Efficacy | | |
|---|---|---|---|
| | RT Alone (n = 31) | RT-Arginine (n = 22) | P value |
| Partial | 4 | 13 | |
| Stable Disease | 2 (7%) | 2 (9%) | |
| Progressive Disease | 22 (71%) | 1 (5%) | 0.002 |

Data presented as number of patients (%).

The invention claimed is:

1. A method of treating cancer in a mammal, the method comprising the steps of:
   administering to the mammal from about 1 min to about 120 min prior to radiation therapy a composition consisting of from about 0.5 gm to about 15 gm of L-Arginine or a pharmaceutically acceptable salt thereof and at least one pharmaceutically acceptable carrier or excipient; and
   administering radiation therapy, wherein the composition is administered once daily on the day of the radiation therapy.

2. The method of claim 1, wherein the mammal is administered from about 2 gm to about 15 gm of L-Arginine or a pharmaceutically acceptable salt thereof prior to the radiation therapy.

3. The method of claim 1, wherein the mammal is administered from about 5 gm to about 15 gm of L-Arginine or a pharmaceutically acceptable salt thereof prior to the radiation therapy.

4. The method of claim 1, wherein the mammal is administered from about 7 to about 15 gm of L-Arginine or a pharmaceutically acceptable salt thereof prior to the radiation therapy.

5. The method of claim 1, wherein the composition is administered from about 5 minutes to about 120 minutes prior to administering radiation therapy.

6. The method of claim 1, wherein the composition is administered from about 5 minutes to about 60 minutes prior to administering radiation therapy.

7. The method of claim 1, wherein the L-Arginine or a pharmaceutically acceptable salt thereof is L-Arginine hydrochloride.

8. The method of claim 1, wherein about 10 gm of L-Arginine hydrochloride is orally administered about 55 to about 65 minutes prior to administering radiation therapy.

9. The method of claim 1, wherein the cancer is bladder cancer, breast cancer, cervical cancer, esophageal cancer, head and neck cancer, laryngeal cancer, lung cancer, ovarian cancer, brain metastases, pancreatic cancer, prostate cancer, rectal cancer, skin cancer, testicular cancer, uterine cancer, or a brain tumor.

10. The method of claim 1, wherein the cancer is brain metastases, breast cancer, brain tumor or lung cancer.

11. The method of claim 1, wherein the cancer is brain metastases.

12. The method of claim 1, wherein the cancer is lung cancer.

13. The method of claim 1, wherein the cancer is breast cancer.

14. The method of claim 1, wherein the composition is administered orally.

15. The method of claim 1, further comprising administering to the mammal a second active ingredient either simultaneously or in parallel with the L-Arginine or a pharmaceutically acceptable salt thereof, wherein the second active ingredient includes one or more of an anti-neoplastic agent, an anti-cancer agent, and an anti-cell proliferation agent.

* * * * *